United States Patent [19]

Wilson et al.

[11] Patent Number: 5,061,619

[45] Date of Patent: Oct. 29, 1991

[54] IMMUNOASSAY USING ANTIBODY-ANTIGEN CONJUGATES

[75] Inventors: Strathearn Wilson, King City; Robert J. Dwyer, Markham, both of Canada

[73] Assignee: Connaught Laboratories Limited, Willowdale, Canada

[21] Appl. No.: 569,776

[22] Filed: Aug. 22, 1990

Related U.S. Application Data

[63] Continuation of Ser. No. 116,880, Nov. 5, 1987, abandoned.

[51] Int. Cl.$^5$ .................. C12Q 1/70; G01N 33/53; G01N 33/543; G01N 33/546
[52] U.S. Cl. .................................. 435/5; 435/7.1; 435/7.9; 435/7.92; 435/7.94; 436/507; 436/509; 436/512; 436/513; 436/518; 436/536; 436/540; 436/820
[58] Field of Search ............... 435/5, 7, 29, 7.1, 7.9, 435/7.92, 7.94; 436/507, 509, 512, 513, 518, 536, 540, 547, 548, 86, 820

[56] References Cited

U.S. PATENT DOCUMENTS

| 3,867,517 | 2/1975 | Ling | 436/531 |
|---|---|---|---|
| 4,197,361 | 4/1980 | Hoff et al. | 435/5 |
| 4,230,683 | 10/1980 | Decker et al. | 436/518 |
| 4,273,756 | 6/1981 | Ling et al. | 424/1.1 |
| 4,486,530 | 12/1984 | David et al. | 435/7.91 |
| 4,746,631 | 5/1988 | Clagett | 436/518 |

OTHER PUBLICATIONS

Wisdom, Clinical Chemistry, vol. 22 (8), pp. 1243–1255 (1976).
Habermann—Z. Clin. Chem. Clin. Biochem., 8, 51 (1970).
Catt and Tregear—Science, 158, 1570 (1967).
Wilson & Logan—Develop. Biol. Standard, vol. 30, pp. 240 to 243 (1975).
Nakane—Journal of Histochemistry and Cytochemistry, vol. 22, pp. 1084 to 1091 (1974).
Hsiung et al.—Journal of Molecular and Applied Genetics, 2:497 to 506 (1984).
Kohler and Milstein—Nature, 256, 495 (1975).

Primary Examiner—Esther L. Kepplinger
Assistant Examiner—Janelle Graeter
Attorney, Agent, or Firm—Sim & McBurney

[57] ABSTRACT

A novel immunoassay techniques is provided which is useful in the detection and determination of antibodies to antigens. Antibodies of all classes to a given antigen or the specific subclass of immunoglobulin to a specified antigen can be detected. A conjugate of labelled antibody and specific antigen is used as the third reagent in a sandwich assay.

17 Claims, 2 Drawing Sheets

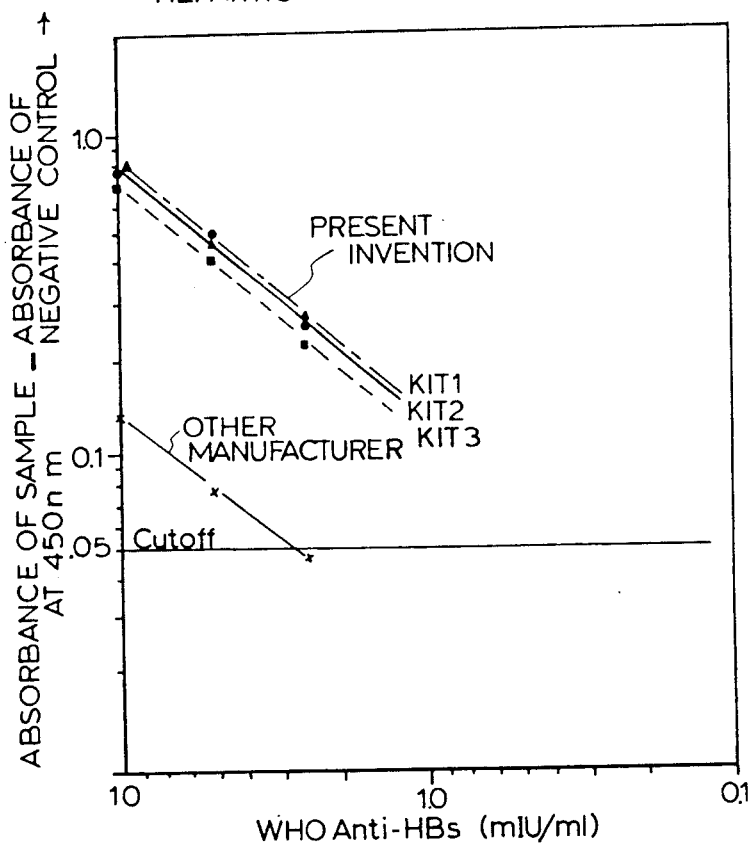
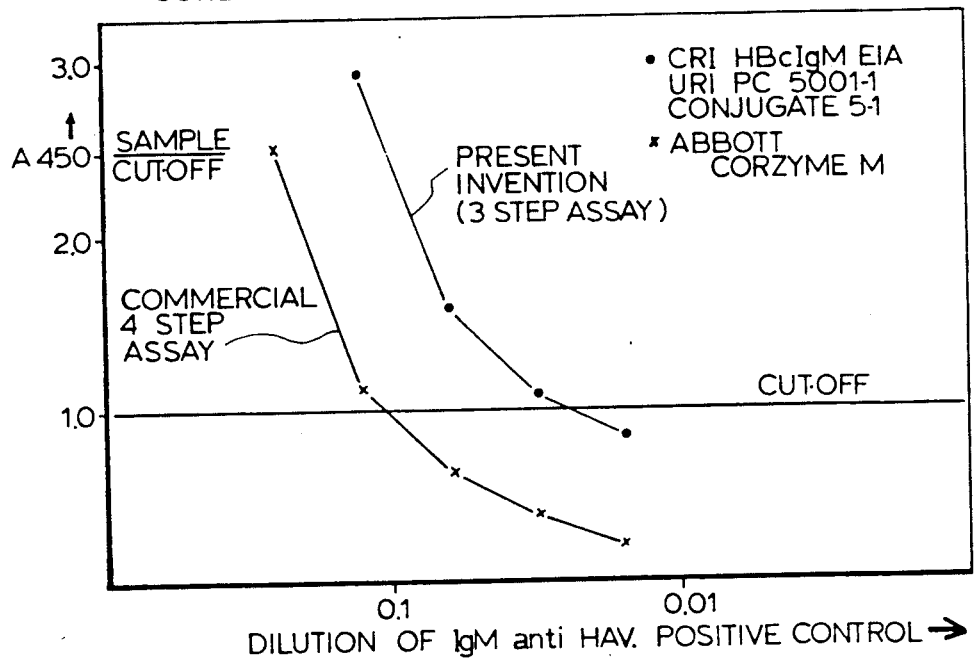

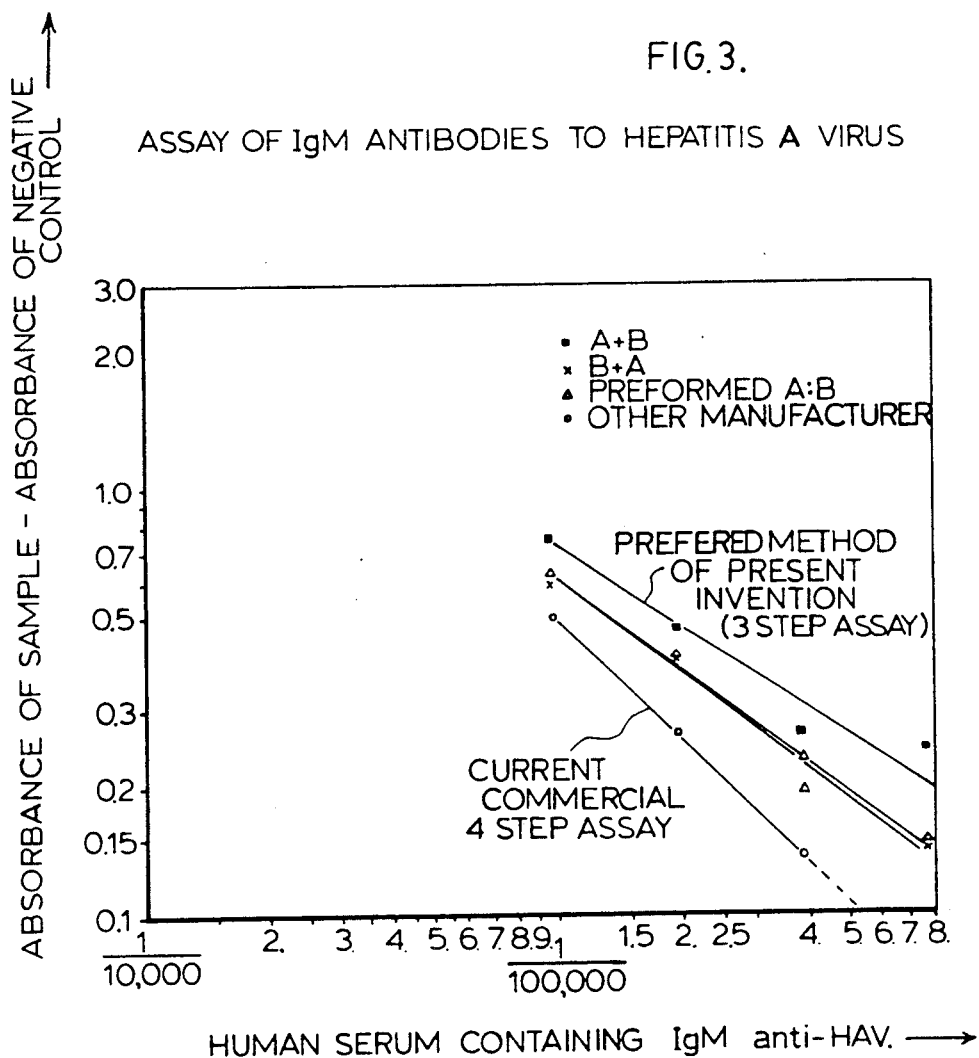

IMMUNOASSAY USING ANTIBODY-ANTIGEN CONJUGATES

This is a continuation of co-pending application Ser. No. 116,880 filed Nov. 5, 1987, now abandoned.

FIELD OF INVENTION

The present invention relates to the detection of materials by the immunoassay method and, in particular, to a novel procedure for effecting the same.

BACKGROUND TO THE INVENTION

One of the most sensitive methods for detecting small quantities of materials, is the immunoassay method, which is based on the combination of the material to be detected, usually called an antigen, and an antibody, raised in an animal, to that antigen. Either the antigen or the antibody is labelled in some fashion to allow for detection. From being a research tool, the method is now used routinely for the screening of large numbers of samples, especially human plasma, for pathogens and foreign substances, such as drugs.

The combination of antigen and antibody, which usually gives a complex of lower solubility than either of the two starting materials, in a test system, is detected by a variety of methods. Initially detection was achieved by radioactively labelling one of the reactants and determining the amount of radiation, either in the separated antigen-antibody complex or in the solution after removal of the complex. More recently detection has been achieved by labelling one of the reactants with an enzyme, which can cause a colour change in the test system, when a substrate is added. A well known example of such an enzyme is horse radish peroxidase, and the test system is known as the enzyme-linked immunosorbent assay (ELISA).

This principle of using an antigen-antibody complex is employed in a number of assays for the detection of pathogenic organisms, or their products, which have invaded a mammalian organism. The method can also be used for the detection of antibodies which the organism has raised to the pathogen. This latter assay is used to determine whether the mammalian organism has been previously exposed to the disease. Examples of these two assays are the detection of the Hepatitis B surface antigen (see, for example, U.S. Pat. Nos. 3,867,517 and 4,197,361) and antibody to this antigen (U.S. Pat. No. 4,230,683).

A number of different types of immunoassay, using the antigen-antibody complex principle, have been developed. One of the most useful immunoassays is the so-called 'sandwich-type' assay, in which one reactant is bound to a solid-phase, for example, a plastic tube, bead or microplate well. This complex is exposed to the second reactant and this mixture, after washing, again is exposed to the first reactant, which has been labelled in some fashion. From this sequence of operations the quantity of the second reactant in the sample can be determined by determining the quantity of labelled material. The second reactant is sandwiched between two layers of the first. Habermann [Z.Clin.Chem.Clin.-Biochem.,8,51,(1970)] used the method for the detection of tetanus toxin present in test samples. The sandwich immunoassay also has been successfully used for the detection of the five different types of antibody present in human and animal sera.

In all the above techniques, the sandwich is built up sequentially by contacting the individual components with the underlying solid-phase for a period of time and then any unbound material is washed off. At no time has a mixture of antibody and antigen been used, since it is generally considered that the formation of the antibody-antigen complex diminishes the immunoreactivity of both components.

SUMMARY OF INVENTION

We have now surprisingly found that macromolecular antigens in combination with their antibodies can be used to form immune conjugates with very little decrease in the immunoreactivity of the antigen. Essential to the present invention is the use of macromolecular antigens which contain multiple copies of epitopes and the use of a limited amount of antibody, which then leaves sufficient epitope sites to react with the solid-phase-bound antibody.

The surprising ability to employ antibody-antigen conjugates in an immunoassay permits labelling of the antibody as the indicator rather than the antigen. Labelling of antigens often can be difficult to achieve and can be ineffective, since antigenic sites are destroyed.

Accordingly, the present invention provides a method of detecting antibodies to antigen, which comprises (a) contacting a solid-phase substrate with an antigen to form a solid-phase substrate antigen complex; (b) contacting the solid-phase complex with a test sample in which the presence of an antibody to the antigen is required to be known; (c) contacting the resulting complex with an antibody-antigen conjugate in which the antibody is labelled with a detectable moiety and the antigen has at least one free antibody binding site in the conjugate; and (d) detecting the presence of the moiety on the solid phase substrate as a detection of the antibody to the antigen in the test sample. The concentration of the moiety on the solid phase substrate may be determined as a measure of the concentration of the antibody to the antigen in the test sample.

The method of the present invention may be used to detect classes and subclasses of antibodies which are specific to a given antigen. A method, in accordance with this aspect of the invention, comprises (a) contacting a solid-phase substrate with an antibody specific for a class or subclass of antibodies to form a solid-phase substrate-antibody complex; (b) contacting the solid-phase complex with a test sample in which the presence of a class or subclass-specific antibody to a desired antigen is required to be known; (c) contacting the resulting complex with an antibody-antigen conjugate in which the antibody is labelled with a detectable moiety and the antigen has at least one free antibody binding site in the conjugate; and (d) detecting the presence of the moiety on the solid phase substrate as a detection of a class or subclass of antibodies which are specific to a given antigen in the test sample. The concentration of the moiety on the solid phase substrate may be determined as a measure of the concentration of the antibody to the antigen in the test sample.

BRIEF DESCRIPTION OF DRAWINGS

FIG. 1 is a graphical representation of results obtained for an assay of antibodies to Hepatitis B surface antigen;

FIG. 2 is a graphical representation of results obtained for an assay of IgM antibodies to Hepatitis B core antigen; and FIG. 3 is a graphical representation of results obtained for an assay of IgM antibodies to Hepatitis A virus.

GENERAL DESCRIPTION OF INVENTION

The present invention encompasses methods for the detection and determination of antibodies to macromolecular antigens. The invention can determine either antibodies of all classes to a given antigen or, with minor modifications, can determine the specific subclass of immunoglobulin to the specified antigen.

For the determination of antibodies to a given antigen, the antigen, or a significant part of it, first is bound to a solid support by adsorption or chemical bonding, to form a complex which will bind antibodies specific to the antigen. This antibody binding "reagent" then is exposed to the test sample containing the antibody to be measured and, after a suitable time, the sample is removed and the test reagent containing bound antibody washed free of test sample. These two steps are the same as those carried out in the conventional sandwich immunoassay procedure.

In accordance with the present invention, the resulting complex then is treated with a conjugate of the macromolecular antigen and a labelled antibody to the antigen.

The conjugate may be preformed by reacting the labelled antibody, which is prelabelled, in accordance with the detection method to be adopted, with the macromolecular antigen by adding solutions one to the other. Alternatively, the conjugate may be formed in situ in the presence of the solid phase complex by the addition of antibody solution and antigen solution in either order. In order to ensure that the conjugate is effective in achieving antigen-antibody binding to the solid-phase-bound sample, the antigen used in the conjugate is macromolecular and has multiple numbers of epitopes and the antibody is used in a ratio which leaves unbound epitopes for binding to the sample.

Generally, there is an optimum ratio of antigen to antibody, depending on the antigen, which will give the best performance in the assay. This optimum is best determined by comparing the sensitivities of mixtures with different proportions of antigen and antibody in the immunoassay. This optimum then is adhered to in subsequent assays for consistent performance. The preferred ratio depends on the antigen but is generally greater than unity.

Following addition of the conjugate of the antigen and a labelled antibody, unbound conjugate is removed by washing and the amount of label, associated with the reacting solid support complex is determined. In our invention, the use of an enzyme labelling system is preferred as a method of determining the concentration of the labelled conjugate, but other methods, such as radioactive labelling, equally may be applied.

In the application of the invention to the determination of the amount of a class or sub-class of antibody to a given antigen that is in a test sample, the first step is the formation of a complex wherein an antibody capable of binding a specific class, or sub-class, of immunoglobulin, such as IgA or IgM, is absorbed onto a solid phase. This specific antibody-binding reagent is contacted with the test sample, and after a suitable time is washed to remove unbound substances. In this way, all antibodies of the appropriate class or sub-class in the test sample are captured by the binding reagent. In accordance with the present invention, the resulting complex then is contacted with the specific antigen-antibody conjugate, formed as described above and containing the labelled antibody, and, after washing, the label amount is measured. This procedure provides the class or sub-class of antibody which is associated with the macromolecular antigen, in the test sample.

The advantages of the present invention are multifold. Firstly, the antigen need not be labelled, rather a complementary antibody is labelled. Many antigens are labile and the purification and labelling processes can destroy antigenic sites, thus decreasing the sensitivity of the reaction. Secondly the assay, as applied to class specific antibodies, can be performed as a three step process, instead of the four step procedure in current practice. These features greatly reduce the time and cost for the immunoassay process, according to the present invention. In addition, the immunoassay technique of the invention exhibits an enhanced sensitivity when compared with conventional immunoassay procedures.

EXAMPLES

EXAMPLE I

This Example illustrates the provision of an assay for all antibodies to Hepatitis B surface antigen.

Preparation of Reagents

Hepatitis B surface antigen (HBsAg) was purified from a pool of human carrier plasma containing the two major sub-types of virus, by standard methods, and used to coat microwells according to the procedures of Catt and Tregear, as published in Science, 158, 1570 (1967). This same HBsAg was used to immunize chimpanzees as described by Wilson and Logan in Develop. Biol Standard, vol. 30, pp. 240 to 243 (1975), from which specific antibody was obtained. The chimpanzee antibodies (anti-HBs) were labelled with the enzyme peroxidase according to the procedure of Nakane as published in the Journal of Histochemistry and Cytochemistry, Vol. 22, pp. 1084 to 1091 (1974).

200 ug of biosynthetic HBsAg (prepared as described in Hsiung et al in Journal of Molecular and Applied Genetics 2:497 to 506 (1984) was incubated with 40 ug of the peroxidase-labelled chimpanzee anti-HBs in 2 ml of phosphate buffered saline at pH 7.4 for 2 hrs. at 37° C. and then diluted to the required concentration (0.125 ug HBsAg/ml) with phosphate buffered saline containing 50% fetal bovine serum, 1.5% normal human serum and 0.01% of gentamicin sulphate.

HBsAg purified from human carrier plasma also has been used successfully formed into a labelled antibody-antigen conjugate and used as a reagent in the assay.

Assay Procedure

Aliquots (0.2 ml) of test and control samples were added to the HBsAg coated microwells and held overnight at room temperature. The wells then were aspirated and washed five times with 0.4 ml aliquots of deionised water. Aliquots of the peroxidase-labelled chimpanzee antiHBs:HBsAg conjugate were added to all the microwells, which then were incubated at room temperature for 4 hours. The wells next were aspirated and washed five times with 0.4 ml aliquots of deionised water. The amount of peroxidase associated with the solid phase was determined by adding 0.2 ml aliquots of the enzyme substrate (0.2 mg/ml of tetramethyl benzidine in dilute hydrogen peroxide) and leaving the mixture in the dark for 30 minutes. It was found convenient to stop the colour reaction by the addition of 0.05 ml of 1N sulphuric acid. The absorption of the solution in each microwell was measured at 450 nm using a microplate spectrophotometer.

The results obtained were plotted graphically and are reproduced in FIG. 1. As may be seen from FIG. 1, the present invention yields an assay with considerably improved sensitivity over a commercial assay where the enzyme is bound to the antigen (HBsAg), using an avidin-biotin linkage. The present invention also shows a much lower false positive rate than commercial radioimmunoassays to detect antibodies against HBsAg.

Similar results are obtained using Hepatitis B core antigen (HBcAg) in place of the HBsAg.

EXAMPLE II

This Example illustrates the provision of an assay for IgM antibodies to Hepatitis B Core Antigen Preparation of Reagents Murine monoclonal antibody specific for the heavy chain of human IgM (M2 antiu) was prepared according to Kohler and Milstein as described in Nature, 256, 495 (1975) and then was used to coat microwells as described in Example I. Biosynthetic Hepatitis B Core antigen (HBcAg) was expressed in E.Coli and purified by standard recombinant technology methods. The immunoglobulin fraction from the plasma of an individual with a high titre of antibodies to HBcAg (defined as anti-HBc) was digested with pepsin, in the conventional manner, to remove the $F_c$ portion of the heavy chains and yield the $(F_{ab})_2$ anti-HBc. This $(F_{ab})_2$ anti-HBc antibody fraction was coupled to peroxidase by the method of Nakane described in Example I. 1.5 ug of the labelled antibody fragment was incubated with 1ug of purified, biosynthetic HBcAg in 2 ml of phosphate buffered saline at pH 7.4 for 2 hours at 37° C. The peroxidase-labelled antibody:antigen conjugate was diluted to the required concentration (0.006 ug HBcAg/ml) by dilution with phosphate buffered saline containing 50% of fetal bovine serum, 10% of normal human serum and 0.01% of gentamycin sulphate.

Assay Procedure

Aliquots (0.2 ml) of test and control samples were added to the M2-antiu coated microwells, which were held overnight at room temperature. The wells were aspirated and washed 5 times with 0.4 ml aliquots of deionised water. The wells were incubated with 0.2 ml aliquots of the labelled antibody:antigen conjugate for 2 hours at 37° C., then aspirated and washed 5 times with 0.4 ml aliquots of deionised water. Aliquots (0.2 ml) of freshly prepared tetramethyl benzidine (0.2 mg/ml) in dilute hydrogen peroxide, were added to all microwells, which then were allowed to stand in the dark for 30 minutes. After the addition of 0.05 ml of 1N sulphuric acid to each well, the absorption of the solution was measured at 450 nm in a spectrophotometer.

The results obtained were plotted graphically and are reproduced in FIG. 2. As may be seen from FIG. 2, the assay of the present invention, involving three incubation steps, is equivalent in performance to a current commercial assay which requires four incubations (as described in U.S. Pat. No 4,273,756).

EXAMPLE III

This Example illustrates the provision of an assay for IgM antibodies to Hepatitis A virus Preparation of Reagents Murine monoclonal antibody, specific for the heavy chain of human IgM (M2 anti-u) was prepared according to the method of Kohler and Milstein described in Example II and was used to coat microwells as previously described.

Antigens from the Hepatitis A virus were obtained by the following method. Human diploid cells infected with the virus in tissue culture, were lysed and the cell supernatant, after centrifugation, was treated with formaldehyde at a dilution of 1:4000 for 3 days at 37° C. to render the mixture non-infective. The inactivated virus suspension was diluted with phosphate buffered saline at pH 7.3 to 25 times the original volume of tissue culture fluid. This solution was designated as Reagent A. The immunoglobulin fraction from the plasma of an individual with a high titre of antibodies to Hepatitis A virus (anti-HAV) was digested with pepsin in the conventional manner to yield the antibody binding fragment $(F_{ab})_2$ anti-HAV. This fraction was coupled to peroxidase as detailed in Example I, and the resulting labelled antibody fragment was diluted 1:6000 in phosphate buffered saline at pH 7.3 containing 10% fetal bovine serum and 4% normal human serum with 0.01% gentamicin sulphate as a preservative. This solution was designated as Reagent B.

Inactivated Hepatatis A virus (Reagent A), diluted 1:2.5 in phosphate buffered saline at pH 7.3 and containing 0.01% gentamicin sulphate, was incubated for 2 hours at 37° C. with the peroxidase labelled antibody fragment, diluted 1:600 in phosphate/saline at pH 7.3 containing 50% fetal bovine serum and 0.01% gentamycin sulphate. This mixture was diluted 1:10 with the same diluent to give Reagent C.

Assay Procedure

Aliquots (0.2 ml) of test and control samples were added to the microwells coated with the M2 anti-u monoclonal antibody. The microwells were held overnight at room temperature and then washed 5 times with 0.4 ml aliquots of deionised water. The microwells then were treated in three different ways with the preformed reagents to assay the IgM antibodies in the sample:

(a) Reagent A (0.1 ml) (known antigen) was added to the wells, followed immediately by Reagent B (0.1 ml) (labelled antibody);

(b) Reagent B (0.1 ml) was added to the wells, followed immediately by Reagent A (0.1 ml); and (c) Reagent C (0.2 ml) (preformed conjugate of Hepatitis A virus antigens and peroxidase labelled human $(F_{ab})_2$ anti-HAV) was added to the microwells.

After the addition of the above reagents, the microwells were incubated for 2 hours at 37° C., and then washed 5 times with 0.4 ml aliquots of deionised water. Aliquots (0.2 ml) of a freshly prepared solution (0.2 mg/ml) of tetramethyl benzidine in dilute hydrogen peroxide were added to all the microwells and the mixtures allowed to stand in the dark for 30 minutes. After the addition of aliquots (0.05 ml) of 1N sulphuric acid, the absorption at 450 nm of the solution in each microwell was measured in a spectrophotometer.

The results obtained were plotted graphically and are reproduced in FIG. 3. It can be seen from the results depicted in FIG. 3 that the assay of the present invention involving three incubation steps, gives a performance superior to a commercial assay using current methodology requiring four incubations (as described in U.S. Pat. No. 4,273,756). It is further evident that all three methods of forming the labelled antibody:antigen conjugate are satisfactory, although the preferred embodiment of the invention is to add the antigen followed by labelled antibody to the microwells (Option [a]), so that the immune conjugate forms at the same time as the solid phase bound IgM antibodies capture the added antigen.

SUMMARY OF DISCLOSURE

In summary of this disclosure, the present invention provides a novel immunoassay procedure using a labelled antibody-antigen conjugate which is beneficial in enabling more sensitive assays to be performed satisfactorily. Modifications are possible within the scope of this invention.

What we claim is:

1. A method of detecting antibodies, which comprises:
   (a) incubating a solid phase with an antigen to form a solid phase-bound antigen,
   (b) washing said solid phase to remove unbound antigen,
   (c) incubating said solid phase-bound antigen with a test sample in which the presence of an antibody to the antigen is required to be known,
   (d) washing said solid phase to remove unbound test sample,
   (e) incubating the resulting complex with an antibody-antigen conjugate in which the antibody is labelled with a detectable moiety and the antigen has at least one free antibody binding site in said conjugate,
   (f) washing said solid phase to remove unbound conjugate, and
   (g) detecting the presence of the moiety on the solid phase as a detection of the antibody to the antigen in said test sample.

2. The method of claim 1 wherein the concentration of the antibody in the test sample is determined.

3. The method of claim 2 wherein said antibody-antigen complex is pre-formed from a macromolecular antigen and labelled antibody and added to said resulting complex.

4. The method of claim 2 wherein said antibody-antigen complex is formed in situ by adding solutions of macromolecular antigen and labelled antibody, in either order, to said resulting complex.

5. The method of claim 1 wherein said antigen contacting said solid-phase substrate is the Hepatitis B surface antigen and said conjugate is a conjugate of the Hepatitis B surface antigen and an antibody to the surface antigen.

6. The method of claim 1 wherein said antigen contacting said solid-phase substrate is the Hepatitis B core antigen and said conjugate is a conjugate of the Hepatitis B core antigen and an antibody to the core antigen.

7. The method of claim 5 wherein said detectable moiety is an enzyme.

8. The method of claim 6 wherein said detectable moiety is an enzyme.

9. A method of detecting classes and subclasses of antibodies, which comprises:
   (a) incubating a solid phase with an antibody specific for a class or subclass of antibodies to form a solid phase-bound antibody,
   (b) washing said solid phase to remove unbound antibody,
   (c) incubating said solid phase-bound antibody with a test sample in which the presence of a class or subclass-specific antibody to a desired antigen is required to be known,
   (d) washing said solid phase to remove unbound test sample,
   (e) incubating the resulting complex with an antibody-antigen conjugate in which the antibody is labelled with a detectable moiety and the antigen has at least one free antibody binding site in said conjugate,
   (f) washing said solid phase to remove unbound conjugate, and
   (g) detecting the presence of the moiety thus associated with the solid phase to detect a class or subclass of specific antibody.

10. The method of claim 9 wherein the concentration of a class or subclass of antibody in the test sample is determined.

11. The method of claim 10 wherein said antibody-antigen complex is pre-formed from antigen and labelled antibody and added to said resulting complex.

12. The method of claim 10 wherein said antibody-antigen complex is formed in situ by adding solutions of antigen and labelled antibody, in either order, to said resulting complex.

13. The method of claim 9 wherein said antibody used in said step (a) is a monoclonal or polyclonal antibody specific for the heavy chain of the IgM class of antibody.

14. The method of claim 9 wherein said labelled antibody is the whole immunoglobulin molecule or the $(F_{ab})_2$ fragment obtained by enzyme digestion of the whole antibody.

15. The method of claim 9 wherein the antibody used in step (a) is to the IgM class of antibodies and the antigen of said antibody-antigen conjugate is Hepatitis A virus.

16. The method of claim 9 wherein the antibody used in step (a) is to the IgM class of antibodies and the antigen of said antibody-antigen conjugate is Hepatitis B core antigen.

17. The method of claim 9 wherein said moiety is a detectable enzyme.

* * * * *